United States Patent
Dal Molin

(10) Patent No.: US 6,539,261 B2
(45) Date of Patent: Mar. 25, 2003

(54) MEASUREMENT OF INTRACARDIAC IMPEDANCE IN A MULTISITE-TYPE, ACTIVE IMPLANTABLE MEDICAL DEVICE, IN PARTICULAR A PACEMAKER, DEFIBRILLATOR AND/OR CARDIOVERTOR

(75) Inventor: Renzo Dal Molin, Chatillon (FR)

(73) Assignee: ELA Medical, S.A., Montrouge (FR)

( * ) Notice: Subject to any disclaimer, the term of this patent is extended or adjusted under 35 U.S.C. 154(b) by 113 days.

(21) Appl. No.: 09/801,268

(22) Filed: Mar. 7, 2001

(65) Prior Publication Data

US 2001/0031995 A1 Oct. 18, 2001

(30) Foreign Application Priority Data

Mar. 7, 2000 (FR) .............................. 00 02879

(51) Int. Cl.[7] .............................................. A61N 1/365
(52) U.S. Cl. .......................................... 607/20; 600/547
(58) Field of Search ................... 600/510, 547; 607/4–6, 9, 17–29, 27–28

(56) References Cited

U.S. PATENT DOCUMENTS

| | | | |
|---|---|---|---|
| 5,501,702 A | 3/1996 | Plicchi et al. | 607/20 |
| 5,522,860 A | 6/1996 | Molin et al. | 607/20 |
| 5,902,325 A | 5/1999 | Condie et al. | 607/28 |
| 6,278,894 B1 * | 8/2001 | Salo et al. | 600/547 |

FOREIGN PATENT DOCUMENTS

EP        0 925 806 A1     6/1999     .......... A61N/1/368

* cited by examiner

Primary Examiner—Kennedy Schaetzle
Assistant Examiner—Kristen Droesch
(74) Attorney, Agent, or Firm—Orrick, Herrington, & Sutcliffe LLP

(57) ABSTRACT

An active implantable medical device, in particular a pacemaker, defibrillator or cardioveter of the multisite type, including a circuit for measuring intercardiac impedance. Electrodes are placed in at least one ventricular site and one atrial site, and are connected to a circuit for the collection of cardiac signals, to detect a depolarization potential, as well as to a stimulation circuit, to apply stimulation pluses to at least some of the aforementioned sites. The measurement of a trans-pulmonary bio-impedance is obtained by injecting a current from an injection circuit (16) between the case (18) of the device and a first atrial (RA−) (or ventricular) site, and measuring a differential potential (20) between the case (18) and a point of measurement located in a second atrial (RA+) (or ventricular) site using a collection circuit. Switches are selectively operable to isolate the case (18) from the current injection and measurement of potential circuits, and to connect them to a common reference potential site, atrial or ventricular (LV−), which is distinct from the sites (RA−, RA+) to which are also connected these circuits, so as to allow a measurement of intracardiac impedance from the signal delivered by the differential potential measuring circuit. The switching is obtained by connections to an electric ground, operating independently of the current injection circuit and the differential potential measuring circuit.

7 Claims, 3 Drawing Sheets

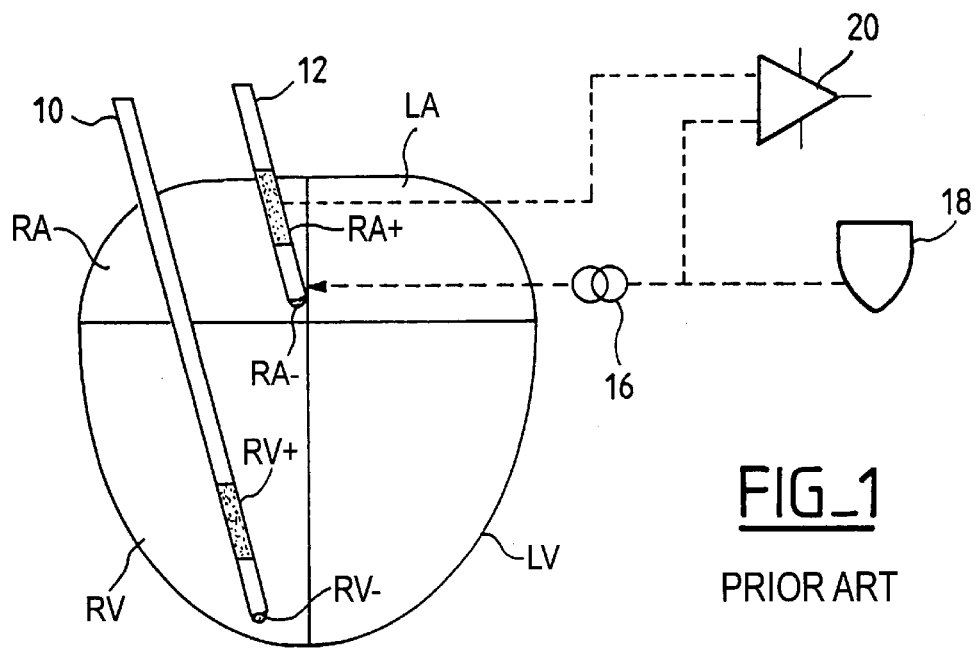
FIG_1
PRIOR ART
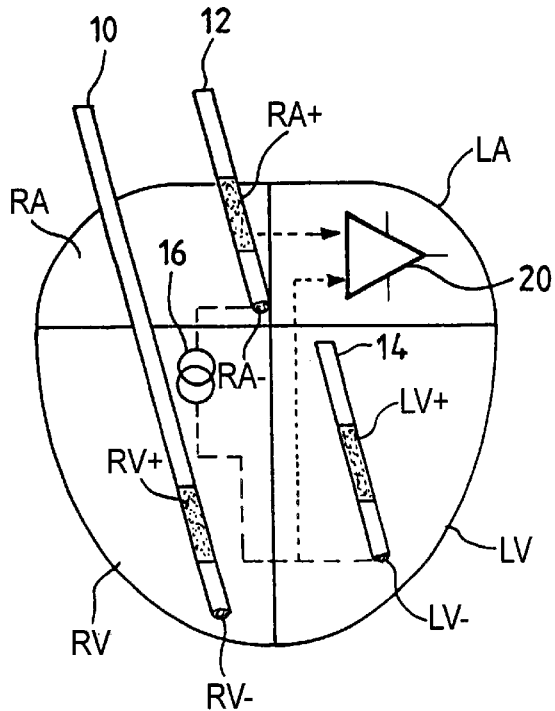
FIG_2
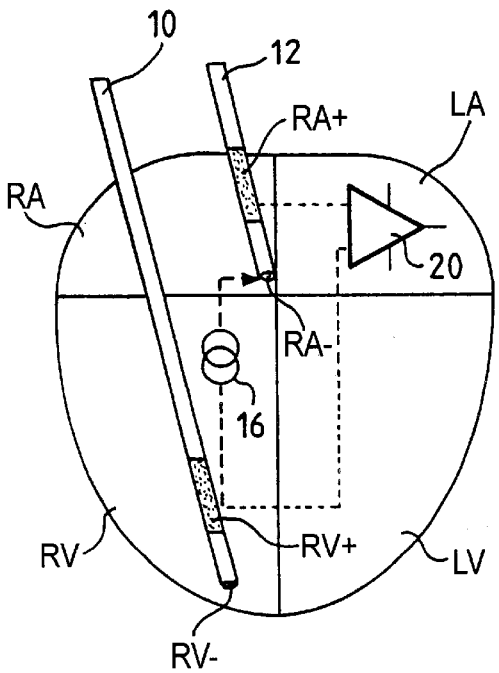
FIG_3

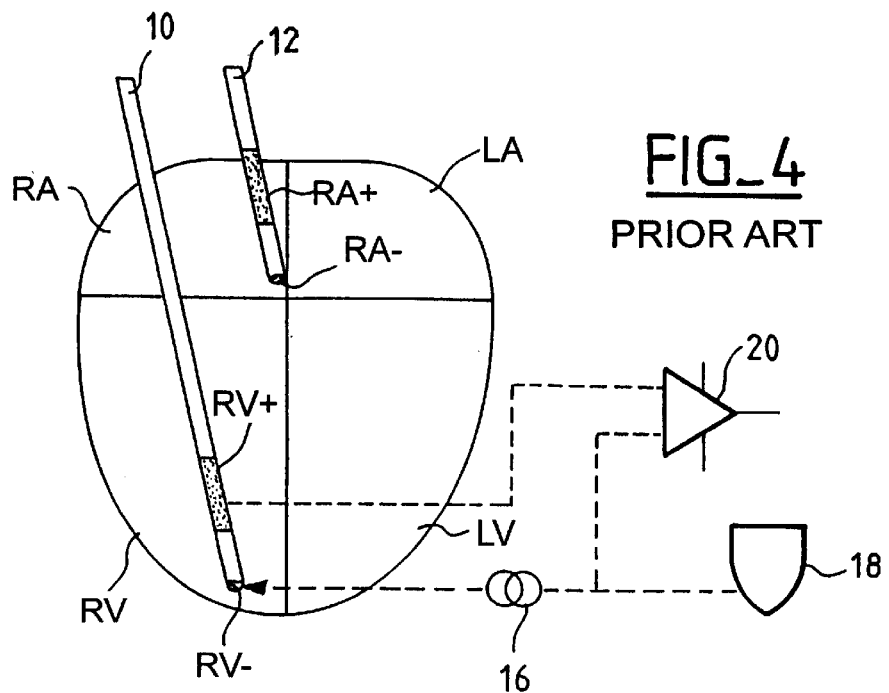
FIG_4
PRIOR ART
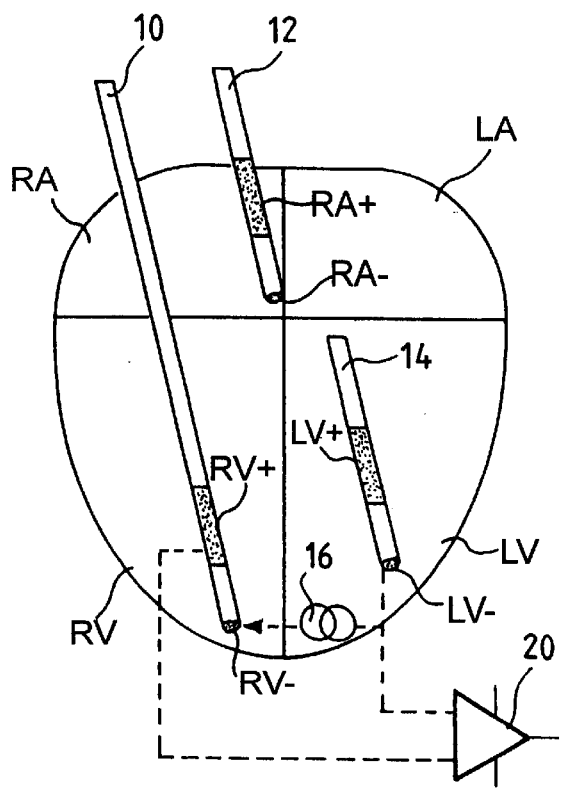
FIG_5
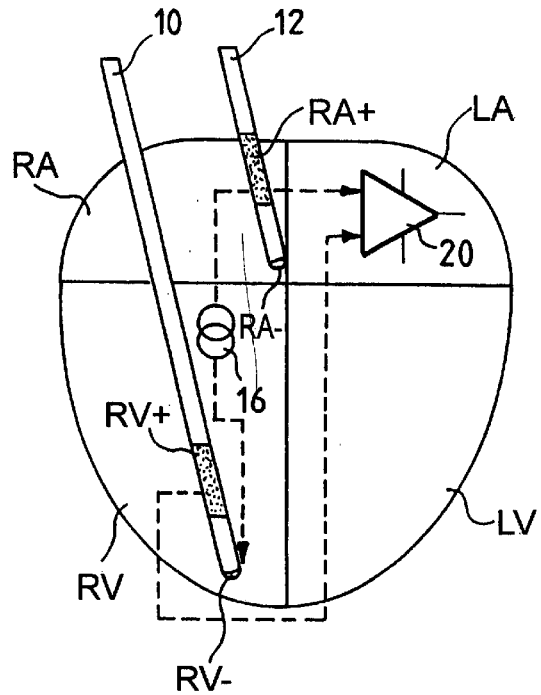
FIG_6

FIG_7
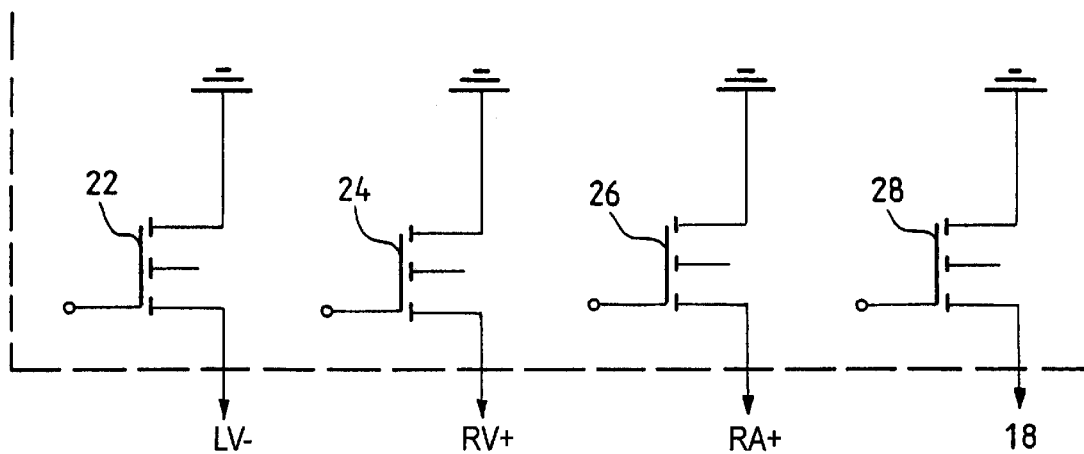
FIG_8
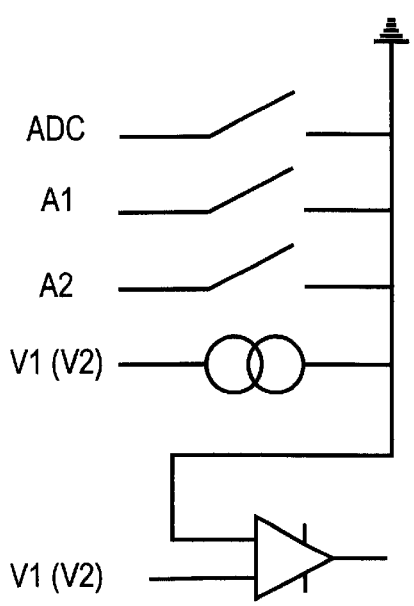
FIG_9
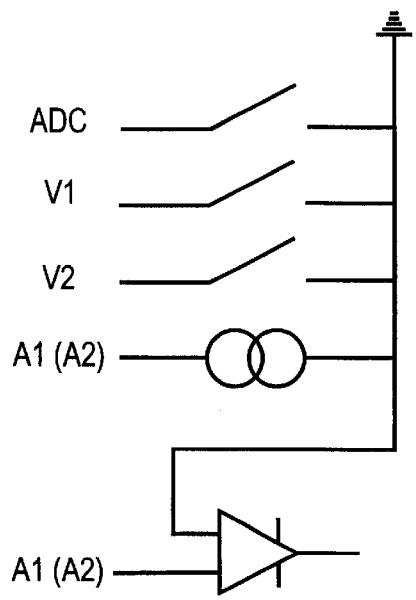

MEASUREMENT OF INTRACARDIAC IMPEDANCE IN A MULTISITE-TYPE, ACTIVE IMPLANTABLE MEDICAL DEVICE, IN PARTICULAR A PACEMAKER, DEFIBRILLATOR AND/OR CARDIOVERTOR

FIELD OF THE INVENTION

The present invention relates to "active implantable medical devices" as such devices are defined by the Jun. 20, 1990 directive 90/385/CEE of the Council of the European Cornmunities, more particularly to pacemaker, defibrillator and/or cardiovertor devices that are able to deliver to the heart stimulation pulses of low energy for the treatment of heartbeat rate disorders. The invention is more particularly directed to the prostheses known as "multisite", in which respective electrodes are placed in a plurality of distinct respective cardiac sites comprising at least one ventricular site and one atrial site. This prosthesis can be of the "double chamber" (right atrial stimulation and right ventricular stimulation) or, generally, "triple chamber" (right atrial stimulation and double ventricular stimulation) or "quadruple chamber" (double atrial stimulation and double ventricular stimulation) type.

BACKGROUND OF THE INVENTION

The control of stimulation implies making an adjustment of various control parameters, such as the stimulation frequency, the atrio-ventricular delay (AVD), or the interventricular delay in the case of a biventricular stimulation.

These various parameters are typically adjusted according to signals delivered by sensors, for example, a minute ventilation (MV) sensor. The minute ventilation is a factor which is representative of the instantaneous metabolic needs of the patient. This factor, in a known manner, is evaluated by measurement of the trans-pulmonary bio-impedance, i.e., between the heart and the case of pacemaker, where the case is located in the top of the thorax. This bio-impedance value is measured by injecting a current pulse between the case and a first cardiac electrode, and collecting (detecting) a signal that is differential potential in response to the current pulse between the case and a second point.

Another factor which is desirable to know is the cardiac flow. It can be interesting, particularly with a multisite pacemaker, to obtain an indication of this flow and thus of the fraction of ejection. The fraction of ejection is the hemodynamic reference parameter used to optimize stimulation on the various cardiac sites. This cardiac flow can be evaluated by measurement of the intracardiac pressure, for example, as proposed in the published application WO-A-99/34863 (Pacesetter AB), but at an expense of requiring a specific probe incorporating a piezoelectric sensor and particular associated electronics to condition the signals resulting from this sensor, to convert them and transmit them to the microprocessor of the pacemaker for processing and use.

Another parameter correlated with the cardiac flow is the transvalvular impedance, a parameter that is generally measured on the right heart, for example, as proposed in U.S. Pat. No. 5,154,171 (Chirife). This document proposes to take the bio-impedance measurement by injecting a current pulse between a ventricular site and an atrial site, and collecting a differential potential between these same two points. In practice, however, it is noted that this configuration (a bipolar configuration of two electrodes) of injection/collection appears sensitive to the movement of the probes containing the electrodes, and does not allow a reliable and precise measurement of the impedance. Moreover, this technique also requires use of a particular electronic circuit to inject the current and collect the signals in response, to convert the collected signals and transmit them for treatment by the microprocessor of the pacemaker.

U.S. Pat. No. 5,501,702 (Plicchi) proposes a configuration that uses the circuits for the measurement of the minute ventilation by intracardiac injection/collection also to perform the trans-pulmonary current injection/signal collection, so as to measure intracardiac bio-impedance values correlated with hemodynamic parameters such as cardiac flow and fraction of ejection. But this known device also uses complex and multiple switching, wherein a particular cathode and anode are connected to switching transistors to ensure the appropriate electric connections between the case and the measuring circuit, the atrial electrodes, and the ventricular electrodes. In fact, these multiple switches involve a system that is so complex a system that in practice it is unrealizable. This is particularly true in a multisite type of device.

OBJECT AND SUMMARY OF THE INVENTION

It is, therefore, an object of the present invention to propose an improved configuration making it possible to adapt the minute-ventilation measuring circuitry to evaluate intracardiac bio-impedances. It is another object to provide such a measuring circuit that minimizes the additional circuitry required and makes the system simple and advantageous to realize.

More particularly, the invention relates to an improvement of a device such as the one described in the Plicchi U.S. Pat. No. 5,501,702 mentioned above, in which electrodes are placed in a plurality of distinct respective cardiac sites comprising at least one ventricular site and one atrial site, these electrodes being connected to a circuit for the collection of cardiac signals, able to detect a depolarization potential, these electrodes also being connected to a stimulation circuit, able to apply stimulation pulses to at least certain ones of the aforesaid cardiac sites.

This device further includes means for assessing the metabolic needs of the patient by measurement of a trans-pulmonary bio-impedance, these means including a circuit for injecting a current between a first output connected to the case of the device and a second output connected to an injection point located in a first atrial or ventricular site, and a circuit for measuring a differential potential generated by the current injection between a first input connected to the case of the device and a second input connected to a measurement point located in a second atrial or ventricular site, respectively.

The device also includes a means for measuring an intracardiac bio-impedance, including commutation (switch) means that is able to isolate the case from the first output of the current injection circuit and from the first input of differential potential measuring circuit, and to connect the first output of the current injection circuit and the first input of the differential potential measuring circuit to a common reference potential site, i.e., an atrial or ventricular site, distinct from the sites to which are connected the second output of the current injection circuit and the second input of the differential potential measuring circuit, so as to allow a measurement of intracardiac impedance from the signal delivered by the differential potential measurement circuit.

According to the invention, the aforementioned switch means includes means for commuting the circuit element (e.g., an input or an output) to an electric ground potential, operating independently of the current injection circuit and the differential potential measuring circuit.

According to various advantageous subsidiary characterstics of the invention, the switch means are also able to modify the cut-off frequencies of a band pass filter used in the differential potential measuring circuit, preferably in the direction of an increase in the measured frequency band. In one embodiment, the common reference potential site is a left ventricular site, and the points of current injection and differential potential collection are located in distinct respective atrial sites, the measured intracardiac bio-impedance being an atrio-ventricular bio-impedance.

In yet another embodiment, the common reference potential site is a right ventricular site, and the points of current injection and differential potential collection are located in distinct respective atrial sites, the measured intracardiac bio-impedance being a transvalvular bio-impedance.

In still another embodiment, the common reference potential site is a left ventricular site and the points of current injection and differential potential collection are located in distinct respective right ventricular sites, and the measured intracardiac bio-impedance being a inter-ventricular bio-impedance.

In still a different embodiment, the common reference potential site is a right atrial site, and the points of current injection and differential potential collection are located in distinct respective right ventricular sites, and the measured intracardiac bio-impedance is a transvalvular bio-impedance.

In the various embodiments, the aforementioned first and second atrial or ventricular sites are defined by a proximal electrode and a distal electrode, preferably a distal tip electrode of the same atrial or ventricular probe, respectively.

BRIEF DESCRIPTION OF THE DRAWINGS

Other features, characteristics, and advantages of the present invention will appear to a person of ordinary skill in the art in view of the following detailed description of preferred embodiments of the present invention, made with reference to the annexed drawings, in which the same numerical and word references indicate similar elements, and in which:

FIG. 1 illustrates a known configuration for measuring the minute ventilation from the atrium;

FIGS. 2 and 3 show modifications of the configuration of FIG. 1 for measurement of an atrio-ventricular impedance and a transvalvular impedance, respectively;

FIG. 4 illustrates a known configuration for measuring minute ventilation from the ventricle;

FIGS. 5 and 6 show modifications of the configuration of FIG. 4 for measurement of an inter-ventricular impedance and a transvalvular impedance, respectively;

FIG. 7 schematically represents the commutation (switch) transistors for the cardiac sites making it possible to carry out, by appropriate programming, the various configurations shown in FIGS. 1 to 6; and FIGS. 8 and 9 are simplified representations of the configuration with switches for commuting elements to ground, operated according to the circuit of FIG. 7.

DETAILED DESCRIPTION INVENTION

FIG. 1 schematically represents a cardiac muscle with its four cavities: right atrium RA, left atrium LA, right ventricle RV and left ventricle LV. A ventricular probe 10 is introduced into right ventricle RV, with an annular proximal electrode RV+ and a distal tip electrode RV−. An atrial probe 12 is introduced into right atrium RA, with a proximal annular electrode RA+ and a distal tip electrode RA−.

If necessary, it can also be envisaged (as shown in FIGS. 2 and 5) to include a probe 14 on the left ventricle LV, for example, to allow a biventricular stimulation (a triple chamber configuration) and/or a probe on the left atrium LA, if one wishes to carry out a collection of signals and/or a stimulation on the two atria in a quadruple chamber configuration.

The electrodes of the probes are connected to a case of an active implantable medical device which involves various detection, stimulation and control circuits, for example, a case of a multisite pacemaker such as that described in the EP-A-0 925 806 (corresponding to U.S. Pat. No. 6,253,106 (ELA Medical), the disclosure of which is incorporated herein by reference), to which one will be able to refer for further details. It will be noted that the device described in this document comprises switching (commutation) transistors allowing one to connect selectively, and according to various possible configurations, various output stages from a pacemaker in a variable and evolutionary way. The switching according to the various desired configurations is operated by a wired digital logic and/or suitable programming of a microprocessor ensuring the control of MOS type transistors.

The configuration (as already known) illustrated in FIG. 1 allows for the measurement of the minute ventilation from the atrium. This measurement is realized by an injection of a current pulse, schematically represented by the current generator 16 between a first atrial site (in the illustrated example, atrial distal tip electrode RA−) and the metal case 18 of the device. The current injected is, for example, a current of 320 $\mu$A delivered in the form of a pulse of 5 $\mu$s width. The differential potential generated by this current pulse is collected (detected) and measured, as schematically represented by operational amplifier 20, between an atrial site (here, the proximal atrial electrode RA+) distinct from the site used (RA−) for the injection, on the one hand, and case 18, on the other hand. The signal thus collected gives, after suitable processing, an indication of the instantaneous metabolic needs of the patient.

One will note that this configuration for measuring the minute ventilation is a tripolar configuration, with one point (the case) common to the current injection and the signal collection, which thus gives here a reference potential for the measurement.

The measuring circuit just described, initially intended for a measurement of the minute ventilation (a trans-pulmonary impedance), in accordance with the present invention, can be used to measure intracardiac impedances. For this purpose, the same tripolar configuration (a common point forming a reference potential, a point of current injection, and a point of signal collection) is preserved, by simply changing the site providing the potential reference. This modification can be done simply by an internal switch with a multisite device, in the manner described in the above mentioned EP-A-0 925 806 and counterpart U.S. Pat. No 6,253,106.

In the case of the embodiment illustrated in FIG. 2, the connection with case 18 is replaced by a connection with a left ventricular electrode, here the left ventricular distal tip electrode LV−. In other words, left ventricular distal tip electrode LV− becomes the reference potential instead of case 18 of FIG. 1. The sites of injection (atrial distal tip electrode RA−) and of collection (atrial proximal electrode RA+), are not modified.

This configuration makes it possible to measure the atrio-ventricular impedance, which is representative of the cardiac flow and can in particular be used to adjust the heart rate, the atrio-ventricular delay, or the inter-ventricular delay in the case o f a biventricular stimulation. The current injected for the measurement of this atrio-ventricular impedance is, for example, a current of 40 $\mu$A delivered in the form of a pulse of 5 $\mu$s width.

In addition, the signal collection is operated in different frequency bands such that a lower frequency is used for the measurement of the minute ventilation, and a higher frequency is used for the measurement of the atrio-ventricular impedance. This modification of the frequency band can result from a displacement of the cut-off frequencies of the filter, which modification is very easy to carry out by software means in the case that the filtering is a digital filtering of the collected signals.

It will be incidentally noted that it is not essential that the ventricular and atrial sites are on the same side of the heart. Thus, in the case of the embodiment illustrated in FIG. 2 described above, it is possible not to have a right ventricular probe, the selected configuration (eventually programmed) being then a right atrium/left ventricle configuration.

In the alternative configuration of FIG. 3, the selected reference potential is a right ventricular electrode, in the example, the right ventricular proximal electrode RV+. In other words, compared to the known configuration of FIG. 1, in the configuration of FIG. 3 the connection with case 18 forming the common point of the tripolar configuration is replaced by a connection with the right ventricular proximal electrode RV+. This configuration makes it possible to obtain a measurement of the transvalvular impedance parameter representative of the fraction of ejection.

FIG. 4 illustrates another known configuration for measuring the minute ventilation. The difference of this configuration as compared to the configuration illustrated in FIG. 1 is due to the fact that the points of injection and collection are located in the right ventricle, instead of the right atrium. The injection is then done between case 18 and the right ventricular distal tip electrode RV−, and the collection between case 18 and the right ventricular proximal electrode RV+. In this configuration, as in the one of FIG. 1, the reference potential (i.e., the common point of the tripolar configuration) is always case 18.

The configuration illustrated in FIG. 5 is the same as the one of FIG. 4, with the difference that the reference potential no longer is case 18, but instead is a left ventricular electrode, in the example, left ventricular distal tip electrode LV−. This configuration allows, in particular, a measurement of the inter-ventricular impedance, which is an important parameter to control the inter-ventricular delay in the case of a biventricular stimulation.

In the alternative embodiment illustrated in FIG. 6, one chooses as reference potential, instead of case 18 as in the configuration of FIG. 4, a right atrial electrode, in the example, the right atrial proximal electrode RA+. This configuration makes it possible to obtain a measurement of the transvalvular impedance, as in the case of FIG. 3, but this measure starting from the ventricle and not from the atrium.

FIG. 7 represents schematically switching (or commutation) transistors, allowing one to carry out by appropriate programming the various configurations of FIGS. 1 to 6 above, simply by connecting certain sites to ground, as follow:

the activation of transistor 22 puts electrode LV− at ground, the activation of transistor 24 puts electrode RV+ at ground, the activation of transistor 26 puts electrode RA+ at ground and the activation of transistor 28 puts case 18 at ground.

The selection of the various configurations can then be operated in the following way, by simple controlling of the transistors, under the control, for example, of a microprocessor or a wired digital circuit logic:

Configuration of FIG. 1: transistor 28 is activated and during the injection the case is connected to electric ground; Configuration of FIG. 2: the transistor 22 is activated and during the injection the electrode LV− is connected to electric ground; Configuration of FIG. 3: the transistor 24 is activated and during the injection the electrode RV+ is connected to electric ground; (for these three configurations, there is an injection on RA− and a collection on RA+).

Configuration of FIG. 4: transistor 28 is activated and during the injection the case is connected to electric ground; Configuration of FIG. 5: the transistor 22 is activated and during the injection the electrode LV− is connected to electric ground; Configuration of FIG. 6, transistor 26 is activated and during the injection the electrode RA+ is connected to electric ground; (for these three configurations, there is an injection on RV− and a collection on RV+).

It will be noted that, for all of the configurations described above, it is possible to reverse the role of the proximal electrodes and the distal electrodes. In addition, the left atrium can be used in the place of the left ventricle, although this choice involves a greater complexity because, in particular, of the necessitated recourse to the use of coronary probes.

FIG. 8 illustrates in a diagrammatic way the configuration, according to the invention, functioning by switching the selected electrode or case to ground. As one can see in FIG. 8, the branches coming from the ventricular electrodes (V1 and V2) and leading to the current injection circuit 16 and the signal collection circuit 20 are not commutated; they only are switched to ground, according to whether one wants to measure the minute ventilation or the impedance, the branches coming from the case (analog-to-digital converter ADC) and from each atrial electrode (A1 and A2), and this commutation is operated very simply by either a connection to ground or an isolation from ground.

FIG. 9 is homologous with FIG. 8, with the roles of the atria and the ventricles having been only reversed.

One skilled in the art will appreciate that the present invention can be practiced by other than the described embodiments, which are presented for purposes of illustration and not of limitation.

I claim:

1. An active implantable medical device, in particular a pacemaker, defibrillator and/or cardiovertor, of the multisite type, having a case, a stimulation circuit able to apply stimulation pulses and a circuit for collection of cardiac signals able to detect a depolarization potential, said circuits being connectable to electrodes to be placed in a plurality of distinct respective cardiac sites comprising at least one ventricular site and one atrial site, wherein the stimulation circuit is able to apply stimulation pulses to at least certain ones of the aforesaid sites, said device further comprising:

means for assessing a patient's metabolic needs by measuring a trans-pulmonary bio-impedance, said assessing means further comprising:

a circuit for injecting a current between a first output connected to the case and a second output connected to a point of injection located in a first atrial or ventricular site, and a circuit for measuring a differential potential between a first input connected to the case and a second input connected to a measurement point located in a second atrial or ventricular site, respectively, the differential potential measured being generated by the current injection;

means for measuring an intracardiac bio-impedance, including switch means having a first state to isolate from the case the first output of the current injection circuit and the first input of the differential potential measuring circuit, and a second state to connect the first output of the current injection circuit and the first input of the differential potential measuring circuit to a common reference potential site, either atrial or ventricular, said common reference potential site being distinct from said atrial or ventricular sites to which are connected the second output of the current injection circuit and the second input of the differential potential measuring circuit, said first and second states allowing measurement of an intracardiac impedance from a signal delivered by the differential potential measuring circuit, wherein said device is characterized in that said switch means further comprises means for selectively commuting one of said case, inputs and outputs to an electric ground, said commuting means operating independently of the current injection circuit and the differential potential measuring circuit.

2. The device of claim 1, wherein said differential potential measuring circuit comprise a frequency band pass filter having at least two cutoff frequencies defining a pass band, and the switch means also is able to modify the cut-off frequencies in a direction to increase the measured frequency pass band.

3. The device of claim 1, wherein switch means is operable to connect the first output of the current injection circuit and the first input of the differential potential measuring circuit to a left ventricular site forming the aforementioned common reference potential site, and connect the second output of the current injection circuit and the second input of the differential potential measuring circuit to distinct respective atrial sites, said intracardiac bio-impedance measured being one of an atrial-ventricular and a transvalvular bio-impedance.

4. The device of claim 1, wherein said switch means is operable to connect the first output of the current injection circuit and the first input of the differential potential measuring circuit to a right ventricular site forming said common reference potential site, and connect the second output of the current injection circuit and the second input of the differential potential measuring circuit to distinct respective atrial sites, said intracardiac bio-impedance measured being a transvalvular bio-impedance.

5. The device of claim 1, wherein said switch means is operable to connect the first output of the current injection circuit and the first input of the differential potential measuring circuit to a left ventricular site forming said common reference potential site, and connect the second output of the current injection circuit and the second input of the differential potential measuring circuit to distinct respective right ventricular sites, said intracardiac bio-impedance measured being an inter-ventricular bio-impedance.

6. The device of the claim 1, wherein said switch means is operable to connect the first output of the current injection circuit and the first input of the differential potential measuring circuit to a right atrial site forming said common reference potential site, and to connect the second output of the current injection circuit and the second input of the differential potential measuring circuit to distinct respective right ventricular sites, said intracardiac bio-impedance measured being a transvalvular bio-impedance.

7. The device of claim 1, wherein said first and second atrial or ventricular sites are defined by a proximal electrode and a distal electrode of a same atrial or ventricular probe, respectively.

* * * * *

UNITED STATES PATENT AND TRADEMARK OFFICE
CERTIFICATE OF CORRECTION

PATENT NO. : 6,539,261 B2
DATED : March 25, 2003
INVENTOR(S) : Renzo Dal Molin

Page 1 of 1

It is certified that error appears in the above-identified patent and that said Letters Patent is hereby corrected as shown below:

Column 3,
Line 64, after "DESCRIPTION" insert -- OF THE --;

Column 5,
Line 64, delete "starting" and insert -- starts -- therefor;

Column 7,
Line 33, delete "comprise" and insert -- comprises -- therefor; and

Column 8,
Line 26, delete "the claim" and insert -- claim -- therefor.

Signed and Sealed this

Fifth Day of April, 2005

JON W. DUDAS
*Director of the United States Patent and Trademark Office*